(12) United States Patent  
Durette

(10) Patent No.: US 7,988,730 B2  
(45) Date of Patent: Aug. 2, 2011

(54) QUASI-SPHERICAL ORBITAL IMPLANT

(76) Inventor: Jean-Francios Durette, Montreal (CA)

( * ) Notice: Subject to any disclaimer, the term of this patent is extended or adjusted under 35 U.S.C. 154(b) by 1655 days.

(21) Appl. No.: 10/711,695

(22) Filed: Sep. 30, 2004

(65) Prior Publication Data

US 2006/0069434 A1    Mar. 30, 2006

(51) Int. Cl.
  *A61F 2/16*    (2006.01)
(52) U.S. Cl. ..................................... 623/6.64
(58) Field of Classification Search ............... 623/4.1, 623/6.64
  See application file for complete search history.

(56) References Cited

U.S. PATENT DOCUMENTS

| | | | |
|---|---|---|---|
| 2,571,721 A | 10/1951 | Jardon | |
| 2,653,327 A | 9/1953 | Allen | |
| 3,070,808 A | 1/1963 | Allen | |
| 4,370,760 A * | 2/1983 | Kelman | 623/6.43 |
| 4,731,077 A | 3/1988 | Allen | |
| 4,976,731 A | 12/1990 | Perry | |
| 5,041,133 A | 8/1991 | Sayano | |
| 5,330,529 A | 7/1994 | Cepela | |
| 5,466,258 A * | 11/1995 | Rubin | 623/6.64 |
| 5,556,427 A | 9/1996 | Durette | |
| 6,063,117 A | 5/2000 | Perry | |
| 6,346,121 B1 | 2/2002 | Hicks et al. | |
| 6,419,698 B1 * | 7/2002 | Finger | 623/6.64 |
| 6,468,313 B1 | 10/2002 | Claeson | |
| 2004/0039445 A1* | 2/2004 | Grip | 623/4.1 |

* cited by examiner

*Primary Examiner* — William H. Matthews
(74) *Attorney, Agent, or Firm* — Brett D. Papendick; Shuttleworth & Ingersoll, PLC

(57) ABSTRACT

A quasi-spherical orbital implant that comprises an off center conical elongation toward its posterior and medial aspects. The conical elongation mimics the natural shape of an orbit. The implant comprises a number of holes and tunnels for suturing the patient's eye muscles and tissue to the implant. A number of hollow voids in the implant serve to progressively host the formation of tissue which secures the implant to the muscles and covering tissue and helps to prevent migration after the sutures have dissolved. The anterior portion of the implant has a number of details which key with the prosthetic eye and help improve its stability and motility.

16 Claims, 18 Drawing Sheets

QUASI-SPHERICAL ORBITAL IMPLANT

BACKGROUND OF THE INVENTION

The invention relates to eye replacement implants. If an eye has become damaged due to trauma or disease, the damaged eye may have to be eviscerated in which all of the inner contents of the eye are removed, or an enucleation may be performed in which the entire eyeball is removed after severing it from the eye muscles and the optic nerve. Following either of these procedures, it is common practice to fill the resulting void with an orbital implant and subsequently fit an ocular prosthesis that closely resembles the eye. After the implant has been inserted into the eye socket following enucleation or evisceration of the eye, tissues heal over the implant. The ocular prosthesis is then placed over these tissues that have healed over the implant. When properly placed within the orbit, the orbital implant replaces some of the volume lost when the eye was removed and helps to maintain the normal structure of the eyelids and eyebrows. When the ocular prosthesis is properly matched to the other eye and coupled to the implant to move with it, substantially normal appearance of the patient is restored.

Eye replacement devices have been available for a number of years to effect functional and cosmetic improvements for the individual who has suffered the loss of an eye. Early ocular implants used in adults were spheres of glass or other inert solid material which filled the orbit, i.e., eye socket, and were then covered with a prosthesis which approximated the curvature and appearance of the human eye. The problem with these devices is that they were smooth on all sides and therefore could not be attached to the extraocular muscles. As a result, the prosthesis would not move with the functioning eye, and would both disconcert a person looking at the wearer and be a source of embarrassment to the wearer.

Another problem with many implants is migration. Migration is the displacement of the implant relative to its proper position in the patient's ocular socket. At times, the migration of an implant may stretch the covering tissue and cause thinning so that the implant surface may become visible or exposed. Many smooth implants migrate because the tissues and muscles of the patient's eye socket are not attached to the implant to hold the implant in its proper place. Even though the implant is buried beneath tissue and muscles, migration, thinning of tissue over the implant, and extrusion of the implant can still occur. Sometimes the tissues which have previously covered the implant become pressured and necrose, thus allowing bacteria to enter and cause infection. This can occur years after the implant is inserted into a patient.

Many current implant devices are intricate non-spherical designs such as the New-Allen, the Universal, and the Iowa. The Universal implant U.S. Pat. No. 4,731,077 is shown in FIG. 13. The problem with non-spherical implants is that a "stock" prosthesis does not properly fit over their non-spherical shape. Although "custom" fitted (non-stock) prosthesis are readily available in many countries, many other countries do not have access to custom fitted prosthesis, and therefore non-spherical implants such as the Universal do not work properly in many areas of the world.

A number of attempts have been made to overcome these and other problems of implant migration. One common attempt is to make the implant porous. Porous implants contain hundreds and often thousands of pores. The porous surface enables living tissue to grow into the pores and help hold the implant in place. However, the rough surface of these implants often cuts and grinds the covering tissue until the implant is exposed, which can cause infection.

Insertion of porous implants into a patient's orbit is difficult because the rough surface of the implant acts like sand paper to the tissue of the patient's orbit. Many porous implants must be wrapped in a smooth plastic covering as they are being inserted into the patient's orbit so that the porous implant does not cling to tissue of the orbit before it is placed deep in the socket. After the porous implant is in place, the plastic sheet is removed from the surface of the implant. If the porous implant is not placed deep within the socket, proper closure of covering tissue will be forceful and may cause early exposure. Once a rough implant is not deep enough, it can't easily be repositioned deeper into the orbit because it clings to the tissue of the orbit. Further, the surgical removal of a porous implant is very difficult (if ever needed) because tissue grows into the thousands of pores on all sides of the implant. Removal of the implant therefore requires the cutting of much tissue which can be a time consuming and damaging process. Many patients' eye sockets have been destroyed by the removal of a porous implant.

Yet another problem with porous implants is the difficulty of curing infections that occur inside the implant. Oftentimes, tissue will not grow into every one of the thousands of pores in a porous implant. If an infection develops in some of the pores that do not have ingrown tissue, then there is no healthy living tissue in the pores to carry medication to the infected site. If medication cannot reach the infected site, it will be impossible to get rid of the infection, and the implant may have to be removed.

U.S. Pat. No. 4,976,731 (Perry) teaches the use of an orbital implant made of a porous material such as hydroxyapatite. Following implantation of porous implants, the patient's tissue grows into the porous structure of the implant as the scleral sac or other covering is absorbed into the system. The '731 patent teaches that after sufficient healing has occurred, the implant can be drilled to provide a passageway that allows the ocular prosthesis to be attached to the implant by insertion of a peg protruding from and forming a part of the prosthesis. The '731 patent asserts that this will resolve the concern of migration or extrusion of the implant because tissue will also grow into and provide a lining for the drilled passageway. However, the procedure of the '731 patent requires a second surgical procedure which comes with the normal risks of such procedures. In addition, complications have been reported with the use of a peg, including infection of the tissue and granuloma formation around the peg implant.

Therefore, there is a need for an ocular implant that is easy to surgically insert and remove from the patient, is totally covered by the patient's tissues, does not need the addition of a peg, yet still has good motility and does not migrate.

SUMMARY OF THE INVENTION

The present invention is a generally smooth surfaced ocular implant device with a quasi-spherical shape. The implant is a quasi-sphere (not a true sphere) because it has an elongated posterior end and an astigmatism with added details anteriorly. The posterior end of the implant is conically elongated off-center, toward the medial side of the implant. The conical elongation helps to keep the entire implant properly aligned because it mimics the natural shape of the bony orbit of the human eye which extends inward (toward the brain), and medially (toward the nasal passage).

The anterior portion of the implant is astigmatic because the medial and temporal portions are bulkier than the superior and inferior portions. The astigmatism makes it more difficult for the prosthesis to undesirably rotate in the orbit. The bulkier medial and temporal portions of the implant stabilize the prosthesis because the astigmatic shape allows the implant to make better contact (key) with the prosthesis than would a spherical implant.

Although the implant is smooth, the anterior portion of the implant has a finite number of holes which lead to tunnels and chimneys. Tunnels are hollow voids which are used for combining the implant to the muscles and tissue covering the implant, preferably by suturing. In addition to receiving the sutures, all of the voids created by the tunnels are adapted for the invasion of body fluids. The tunnels progressively host the formation of new tissue which secures the implant to the muscles and covering tissue to prevent migration. Chimneys are also voids within the implant that host the invasion and formation of tissue to secure the implant within the orbit.

The anterior portion of the implant has a number of mounds and valleys. The mounds protrude away from the surface of the quasi-spherical implant so as to key with the prosthetic eye and provide improved motility of the prosthetic eye. The valleys provide an area into which the eye muscles and tissue can be placed so they can better grip the implant during muscle movement, which also improves motility.

DESCRIPTION OF THE PREFERRED EMBODIMENT OF THE INVENTION

Figure 1:
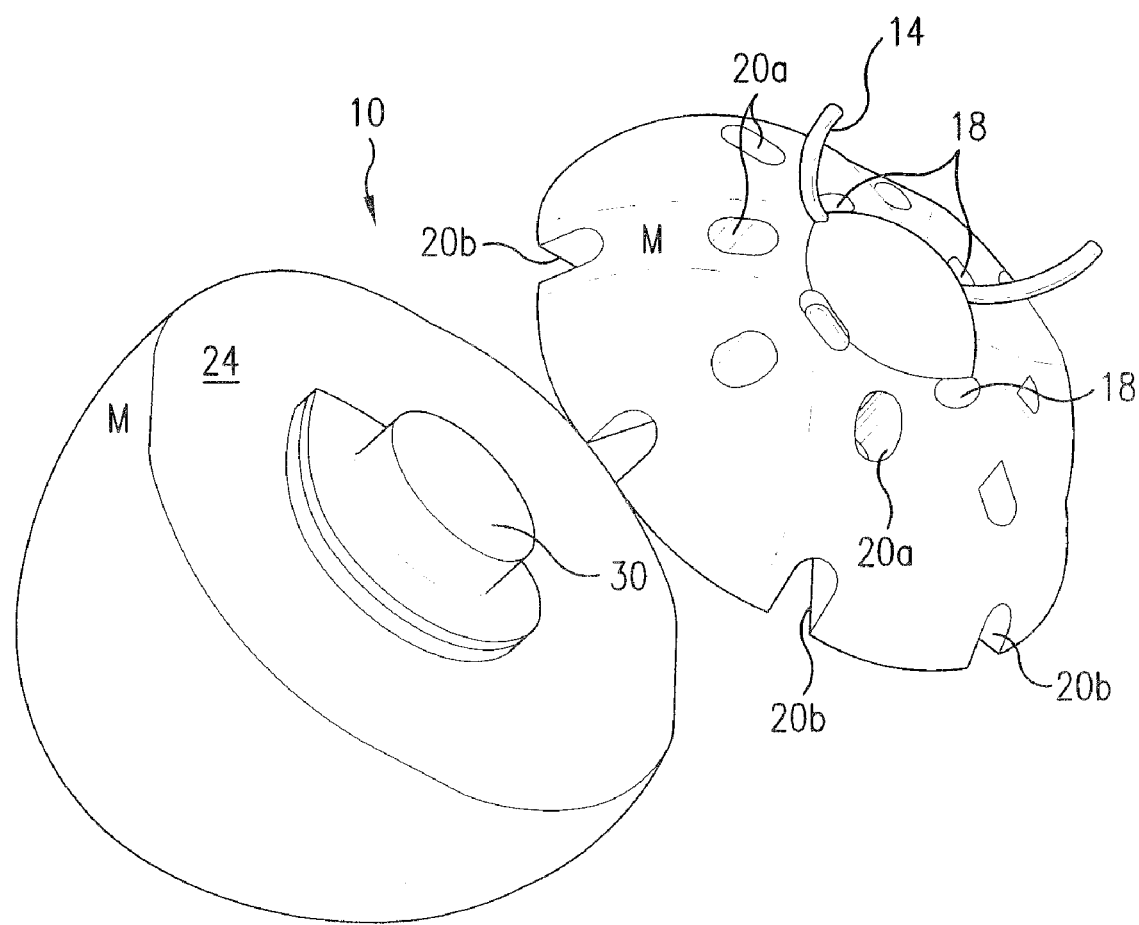
FIG. 1 is a perspective view of the first embodiment of the present invention showing the separate anterior and posterior pieces of the device.
Figure 2:
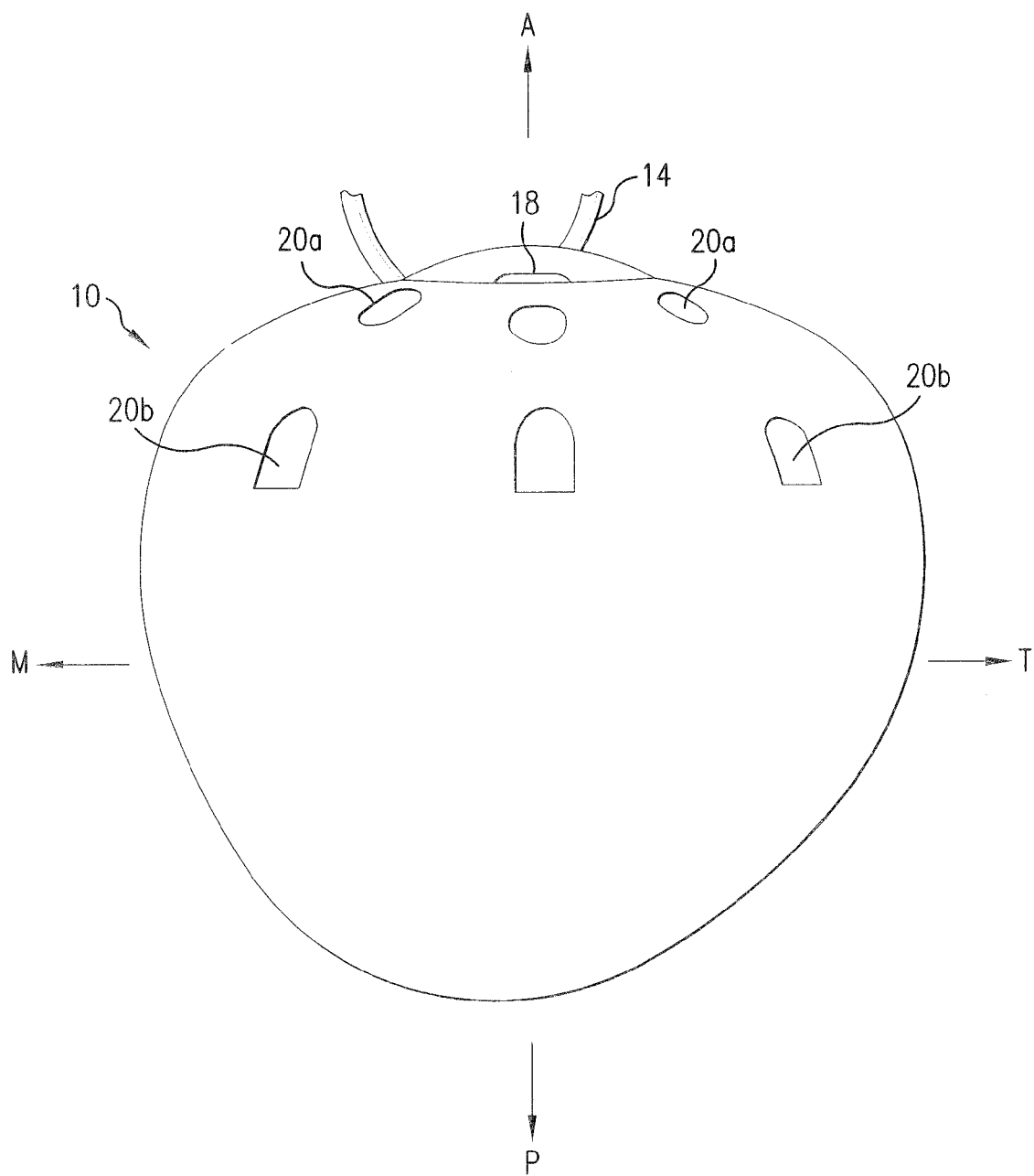
FIG. 2 is a top view of the implant (with reference to its position in a patient's right orbit) showing the conical elongation of the device both posteriorly and medially.
Figure 3:
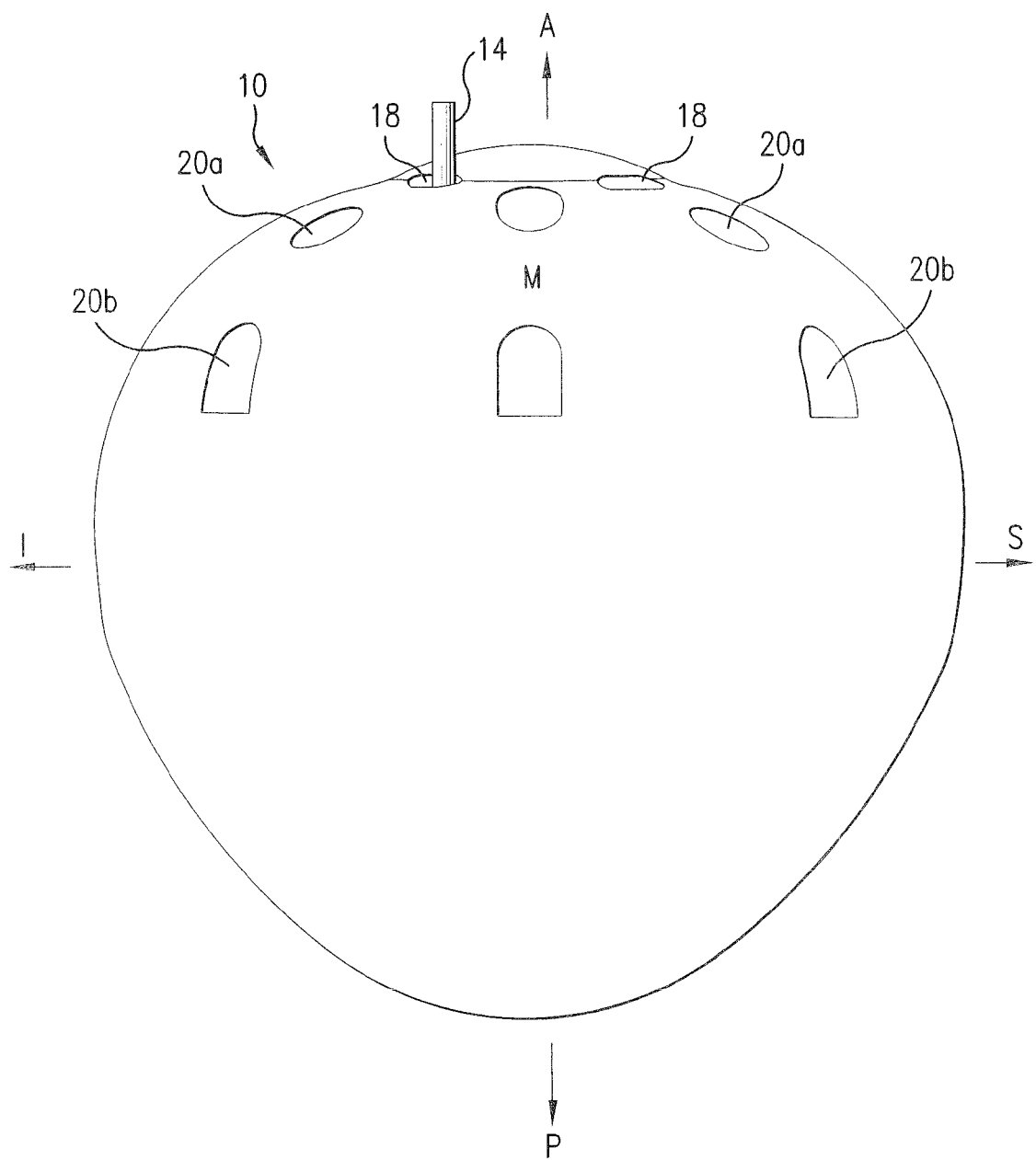
FIG. 3 is a side elevational view of the implant (with reference to its position in a patient's right orbit) showing the "M" which marks the medial side of the device.

As seen generally in FIG. 1, the ocular implant 10 of the present invention comprises an anterior portion 22 and a posterior portion 24. Although the implant 10 may be manufactured as one piece, the preferred embodiment requires the implant 10 to be manufactured as two separate pieces. The two pieces 22, 24 will be collectively referred to as the implant 10. As seen in FIG. 3, the anterior portion 22 comprises a finite number tunnels 18, chimneys 20a, 20b, valleys 11, and mounds 12. Cumulatively, the valleys 11 and mounds 12 are herein referred to as details. It should be noted that the terms anterior A, posterior P, medial M, temporal T, superior S, and inferior I all describe the implant 10 as it is properly positioned in a patient's right orbit with the anterior portion 22 facing out of the patient's orbit. These respective directions can be seen in FIGS. 2 and 3. FIG. 2 is a top view of the implant 10 as it sits in a patient's right orbit showing the anterior (front) A, posterior (back) P, medial (toward nasal) M, and Temporal (toward temple) T directions, respectively. FIG. 3 is a side view showing additional superior (top) S and inferior (bottom) I directions, respectively.

Figure 4:
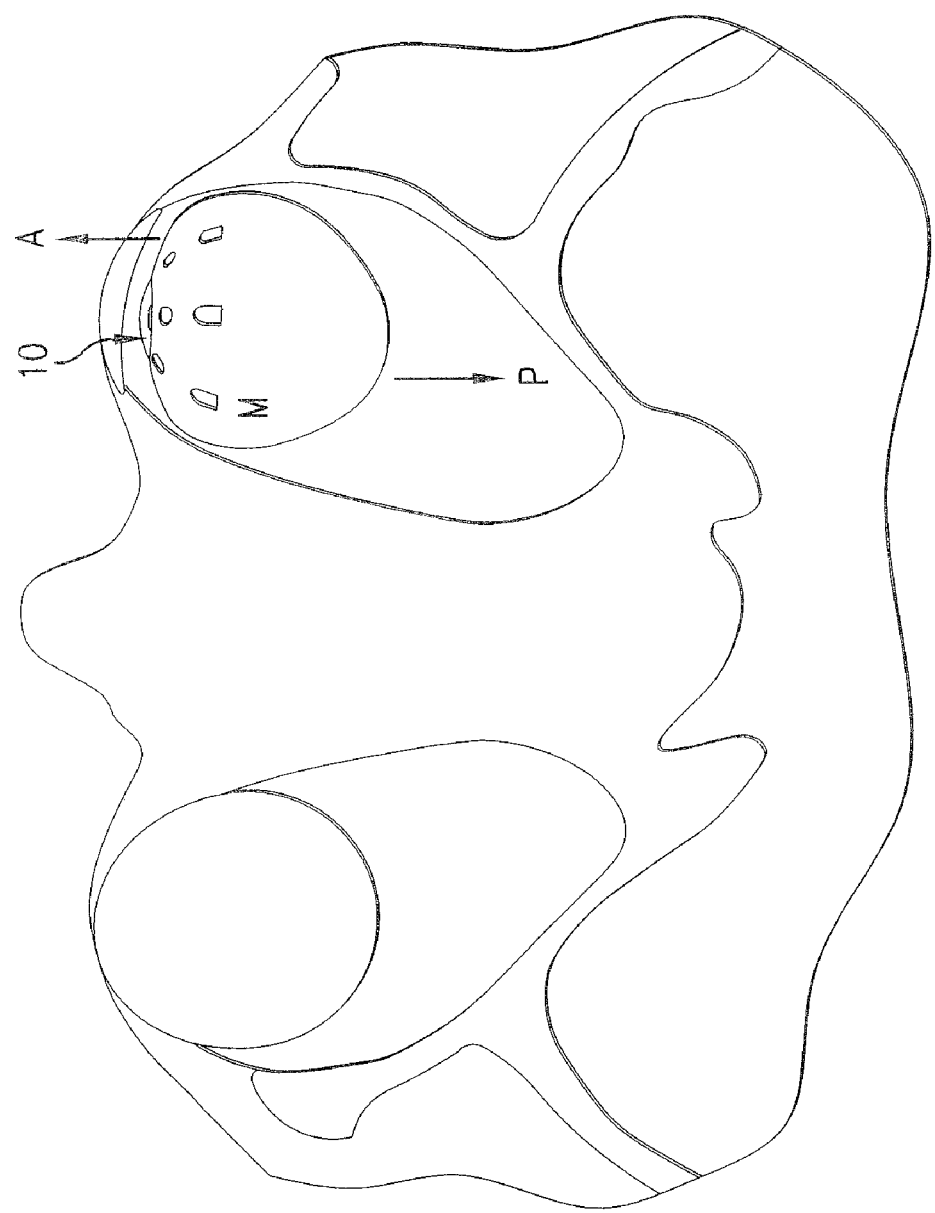
FIG. 4 is a top view showing the relationship of the brain, orbits, and nose in a human head, the implant is properly oriented in the right orbit.
Figure 5:
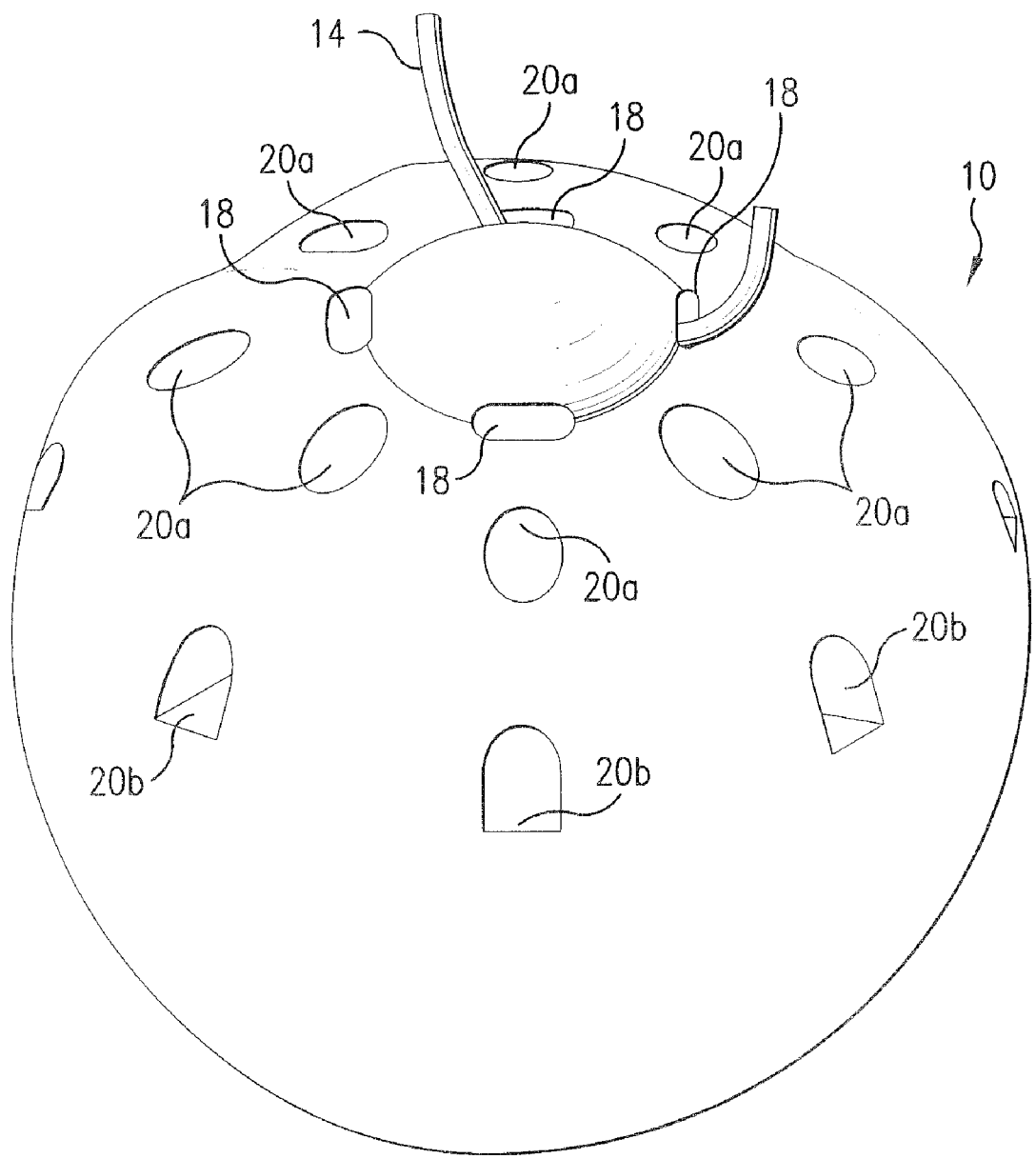
FIG. 5 is a prospective view of the implant of the first preferred embodiment.

As seen in FIG. 2, the shape of the implant 10 of the present invention is quasi-spherical in that there is some conical elongation of the sphere posteriorly P. This conical posterior P elongation is off-center toward the medial M side of the implant 10. FIG. 4 shows the positioning of the implant 10 in a patient's orbit wherein the conical elongation extends posteriorly P and medially M as the implant 10 sits in the orbit, i.e., the conical elongation extends toward the back of the patient's orbit and toward the nasal passage of the patient. This posterior P, medial M elongation helps to align the implant 10 within the patient's orbit so that the implant 10 maximizes its volume inside the vacant orbit. This volume maximization occurs because, as seen in FIG. 4, the natural shape of the orbit extends posteriorly P and medially M. In addition to filling volume in the orbit, the off-center conical elongation also helps to position the details of the anterior portion 22 in the normal direction of the iris because the conical elongation will naturally remain in the posterior P and medial M area of the orbit where it is most comfortable. This greatly reduces the possibility that the anterior portion 22 will become tilted upward and/or outward.

Figure 15:
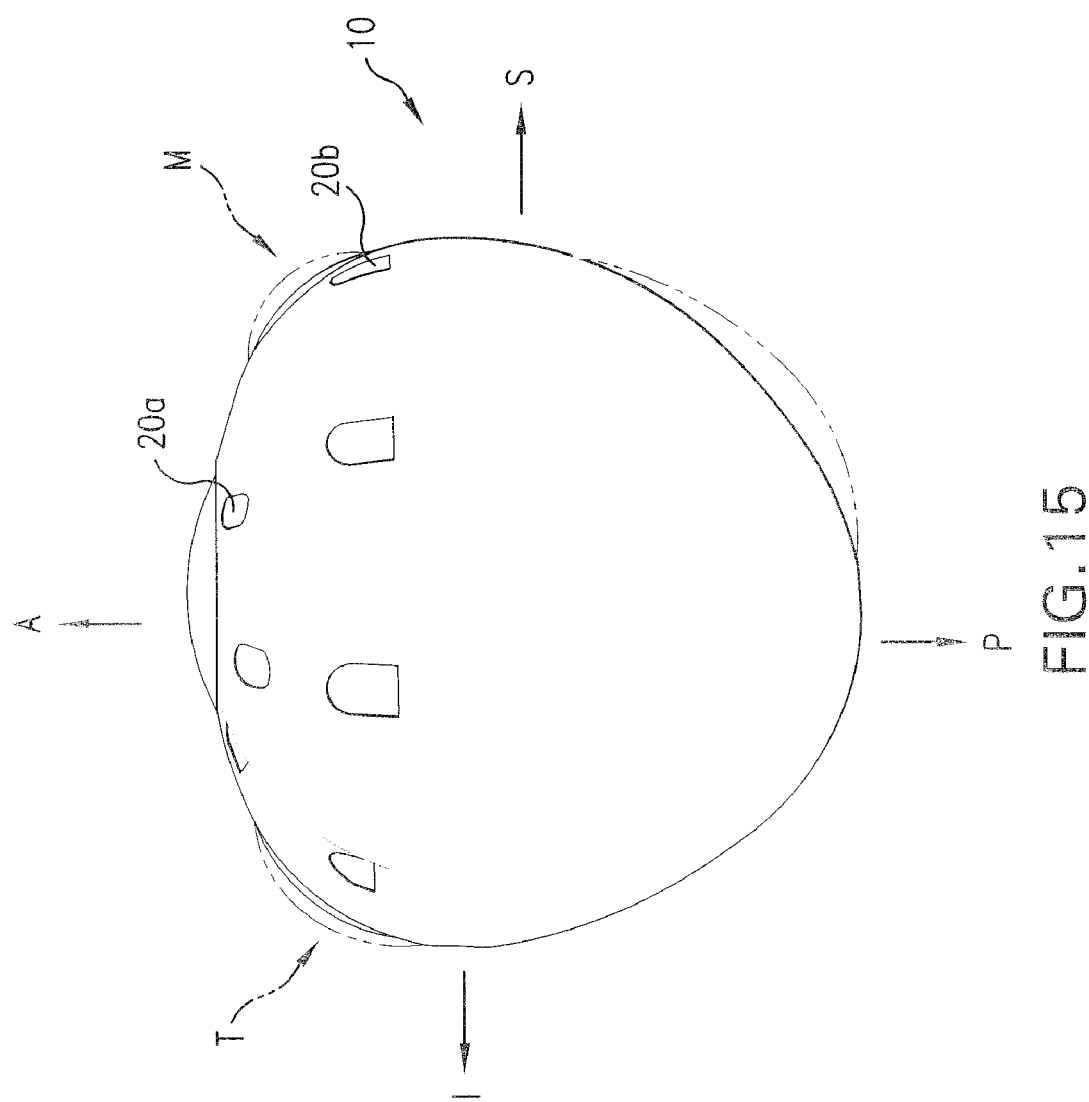
FIG. 15 is a comparative view showing the astigmatic shape of the implant wherein solid lines show the implant lying on its side with the superior side of the implant facing toward the right of the figure, and phantom lines show the implant with the medial side of the implant facing toward the right of the figure.

The anterior portion 22 of the implant 10 has an astigmatic shape. The astigmatic shape is best seen in FIG. 15 which shows that the implant 10 is slightly bulkier medially M and temporally T, while it is less bulky superiorly S and inferiorly I, i.e. the radius of the quasi-sphere implant 10 is longer toward the medial M and temporal T areas of the anterior portion 22, and shorter toward the superior S and inferior I areas of the anterior portion 22. FIG. 15 is a comparative view showing the astigmatic shape of the implant 10 wherein solid lines show the implant lying on its side with the superior S side of the implant being toward the right of the figure, and phantom lines show the implant 10 with the medial M side of the implant 10 toward the right of the figure. In the anterior portion of FIG. 15, the phantom liners of the medial M and temporal T sides of the implant 10 protrude beyond the solid lines of the superior S and inferior I sides. This astigmatic shape helps to provide motility for the prosthesis because the shape keys with the prosthesis. The keying provided by the astigmatic shape of the implant 10 also helps to prevent the involuntary rotation of the impression-fitted prosthesis, which is often embarrassing for the patient.

It is important that practitioners correctly orient the conical elongation and astigmatic shape of the implant 10 inside the patient's orbit. As seen in FIG. 3, to help practitioners, the preferred embodiment of the invention comprises the letter "M" on the medial M side of the implant 10 to notify practitioners that side of the implant 10 faces toward the medial M side of the patient's orbit.

Figure 13:
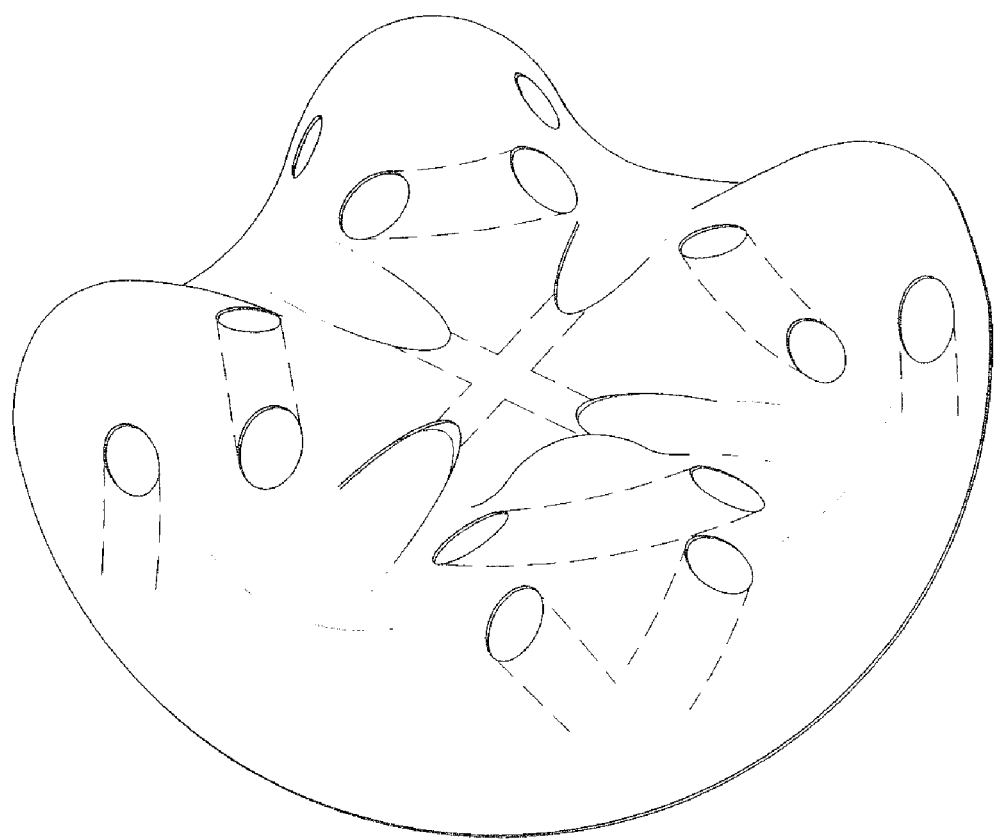
FIG. 13 is a perspective view of a prior art implant device.

The details, i.e. valleys 11 and mounds 12, on the anterior portion 22 of the implant 10 key with the prosthesis so as to provide good motility for the prosthesis. The keying effect is produced as the valleys 11 and mounds 12 gently contact the prosthesis thereby causing it to move. The details on the anterior portion 22 are not so pronounced that they take away from the generally spherical shape of the implant. It is important that the implant 10 remain mostly spherical because, as discussed above in the "Background" section of this specification, non-spherical implants such as the prior art implant device shown in FIG. 13 do not fit properly with stock (non-custom fit) prosthesis.

Although the implant 10 is described below with reference to two specific embodiments comprising different materials, the present invention can be made of any biocompatible implant material. The outer surface of the implant 10 is preferably smooth. The smooth outer surface of the implant 10 does not cling to the patient's tissue, which is beneficial when surgically inserting and removing the implant 10. The smooth surface of the implant 10 of the present invention will minimize aggression from the aging and ill-fitting prostheses on the covering tissues as well as minimize the possibility of late exposures and extrusions.

In the preferred embodiment, the present invention is manufactured in two separate parts and then assembled before implantation into a patient's ocular orbit. In use, after the implant 10 is placed in the patient's orbit, the practitioner will place and suture muscles and covering tissue over the implant 10 so that the implant 10 does not contact the outside air, which could cause infection. The anterior portion 22 of the implant 10 has several valleys 11 and mounds 12. The valleys 11 provide an area into which the eye muscles and tissue can be placed to provide traction for the eye muscles to improve motility of the implant 10 and the prosthesis as the implant 10 keys with the prosthesis.

The anterior portion 22 of the implant has a finite number of openings such as tunnels 18 and chimneys 20a, 20b. The tunnels 18 allow for insertion of a needle and suture. Preferably, the diameter of the tunnels 18 is between one and two millimeters. This is wide enough for most popular suture needles to pass easily. Because of this relatively large tunnel 18 diameter, it is easy to incise the ingrown tissue junctions and sutures to free the implant, if ever surgically needed. The sutures 14 are threaded through the central tunnels 18 for securing the implant 10 to the patient's eye muscles, which have been placed over the implant 10.

In addition to receiving the sutures 14, the voids created by the tunnels 18 are adapted for the invasion of body fluids. The tunnels 18 progressively host the formation of new tissue which secures the implant 10 to the muscles and other tissue. The anterior portion 22 of the implant 10 comprises chimneys 20a, 20b (similar to tunnels 18 but generally do not receive any sutures 14) which are also adapted for the invasion of body fluids so that they progressively host the formation of new tissue which secure the implant 10 to the muscles and other covering tissue. The sutures 14 prevent the implant 10 from migrating or dislodging for a period of time after insertion into the orbit. The sutures 14 become weak and dissolve eight to twelve weeks after implantation, but by then the patient's new tissue has invaded the voids, and adhered to the muscles and the implant 10 to prevent migration.

In addition to preventing migration, the new tissue ingrown within the tunnels 18 and chimneys 20a, 20b have adhered to the muscles and covering tissues, which makes for good motility of the implant 10 in the patient. The valleys 11, mounds 12, and other details on the anterior portion 22 help to key the prosthesis so that the movement of the patient's prosthetic eye looks as natural as possible.

Figure 16:
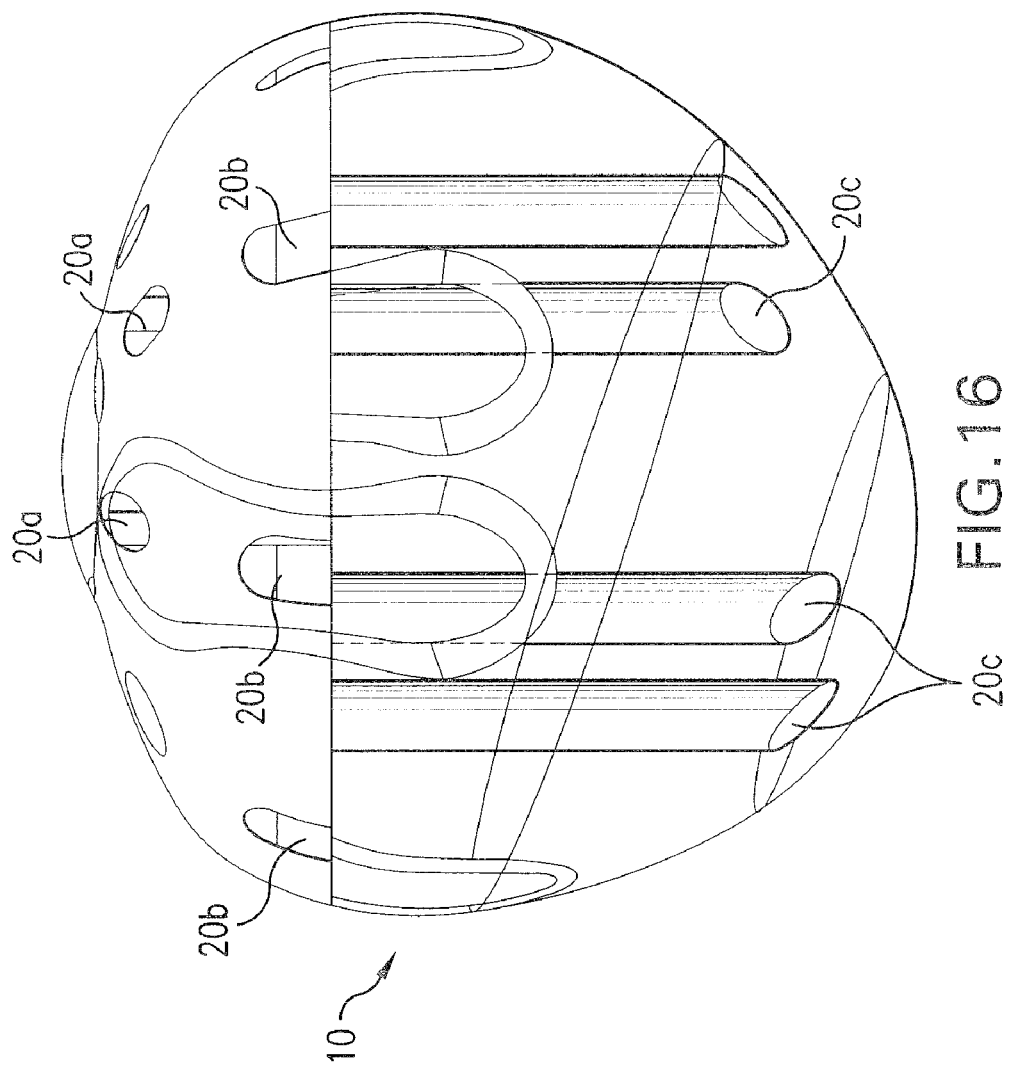
FIG. 16 is a perspective view of the implant with the posterior portion cut away to show the chimneys in the posterior portion.
Figure 17:
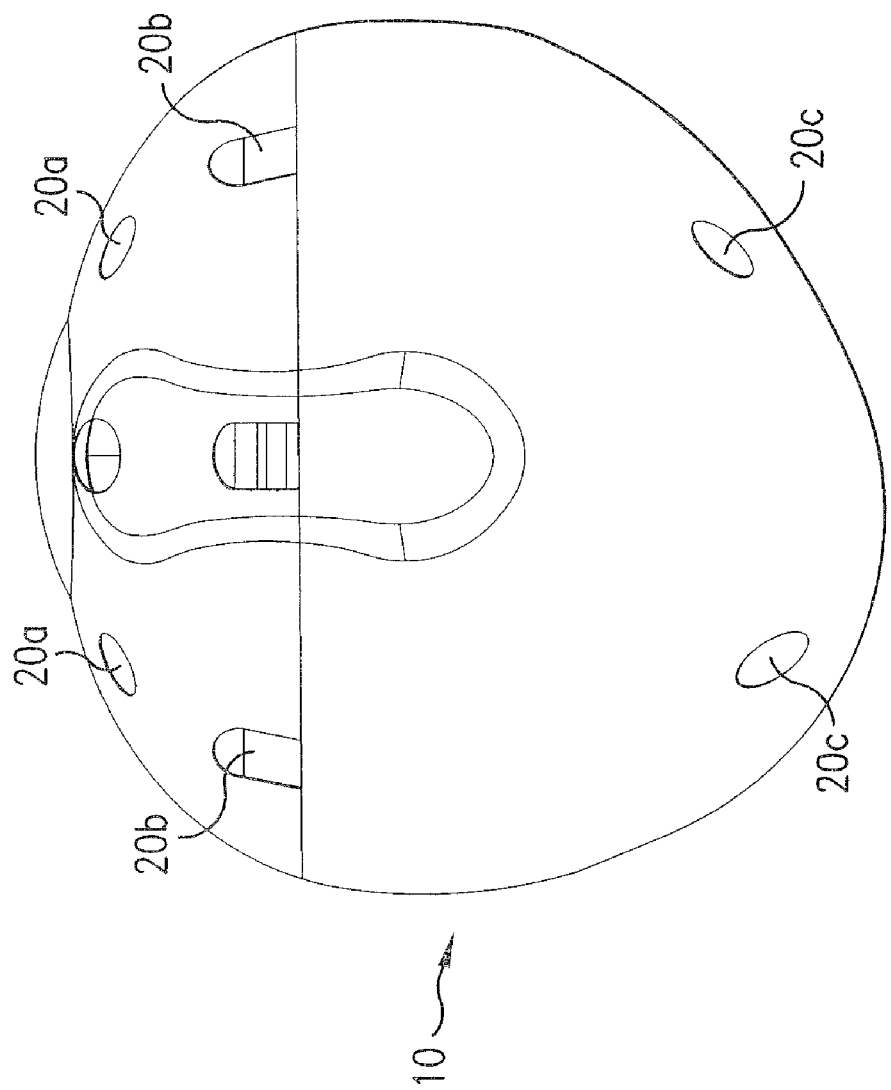
FIG. 17 is a side view of the implant showing the chimneys in the posterior portion.

An alternate embodiment is shown in FIGS. 16 and 17 wherein chimneys 20c are located in the posterior portion 24 of the implant 10 in addition to the chimneys 20a, 20b in the anterior portion 22. These additional chimneys 20c in the posterior portion 24 allow more tissue in growth with the implant 10 so as to better secure the implant 10 to the patient.

It should be noted that the scope of this invention is not limited to a specific number of tunnels 18 and chimneys 20a, 20b on the anterior portion 22 of the implant 10 even though specific numbers are provided below with respect to the preferred embodiments. As one skilled in the art will recognize, the number of tunnels 18 and chimneys 20a, 20b can be modified to accommodate a variety of patients which may have different medical needs.

First Preferred Embodiment

Figure 6:
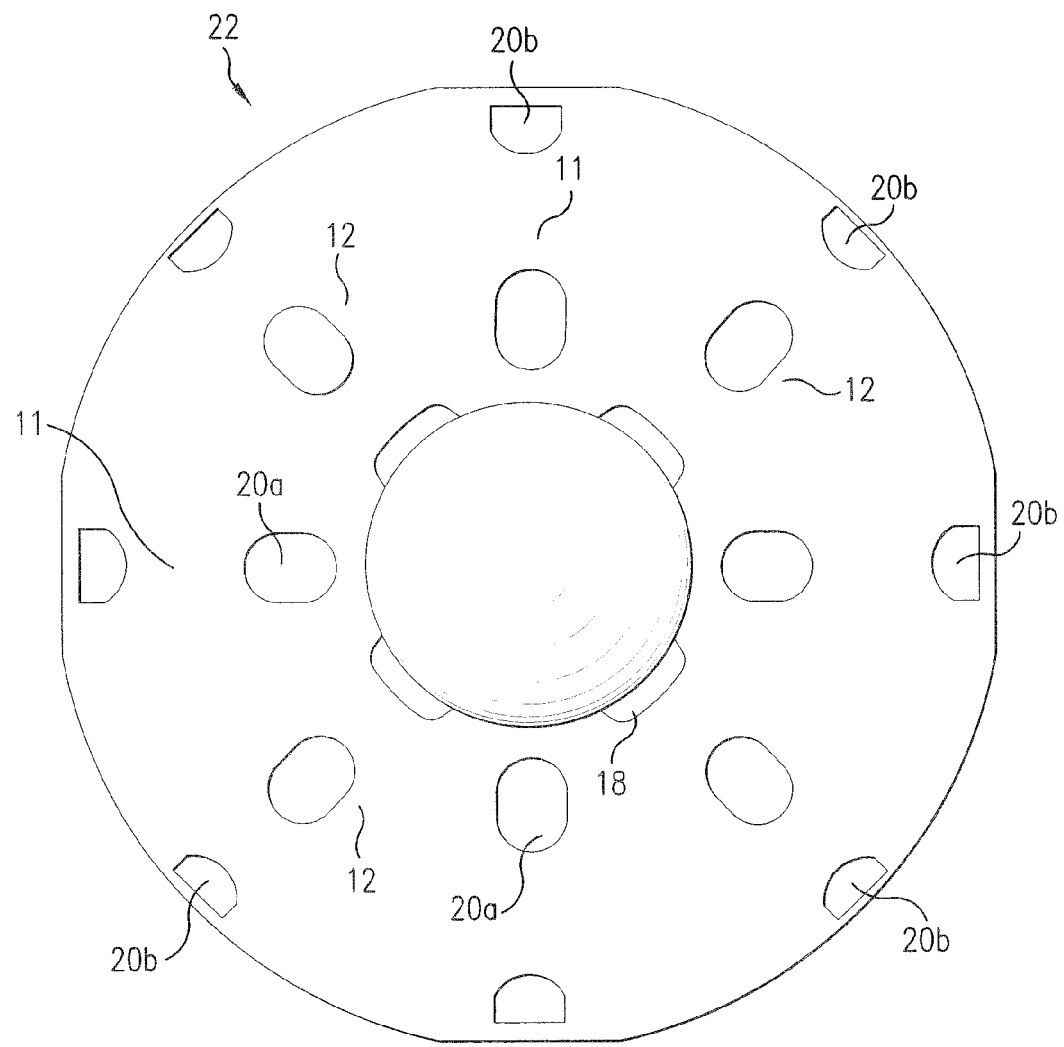
FIG. 6 is a side elevations view of the anterior piece of the implant of the first preferred embodiment (with reference to its position in a patient's right orbit)
Figure 7:
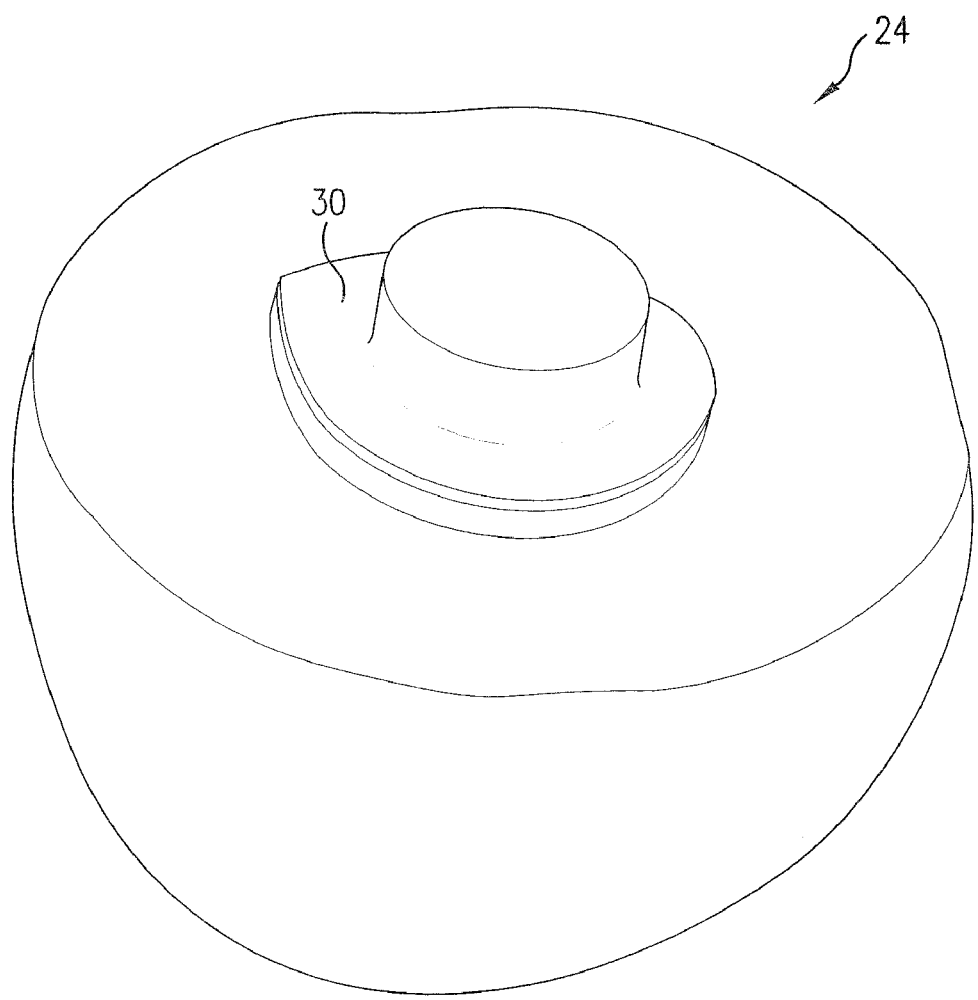
FIG. 7 is a perspective view of the posterior portion of the implant of the first preferred embodiment showing the raised surface that is keyed into the anterior portion.

FIGS. 1 and 5-8 show a first preferred embodiment of the present invention which comprises all the general features described above in addition to the specific features described below. The first preferred embodiment is comprised of a polymer such as acrylic. As described above, the implant 10 is preferably manufactured in two pieces 22, 24. The two pieces 22, 24 are then combined by any suitable means. The preferred means of assembling the two pieces 22, 24 for the acrylic implant 10 is ultra-sonic welding, which is known in the art. As shown in FIGS. 1 and 7, there is an elevated portion 30 on the surface of the posterior portion 24. This elevated portion 30 is adapted for insertion into a correspondingly shaped indentation (not shown) on the underside of the anterior portion 22. The elevated portion 30 is preferably semi-elliptical; however it can be any shape as long as the two portions 22, 24 can only fit together when the portions 22, 24 are orientated in their proper position. The elevated portion 30 assures that the pieces 22, 24 are only welded together when they are properly aligned, which ensures that the "M" (medial) marking is correct and the conical elongation and astigmatic shape of the implant 10 is proper when placed in a patient's orbit.

Figure 8:
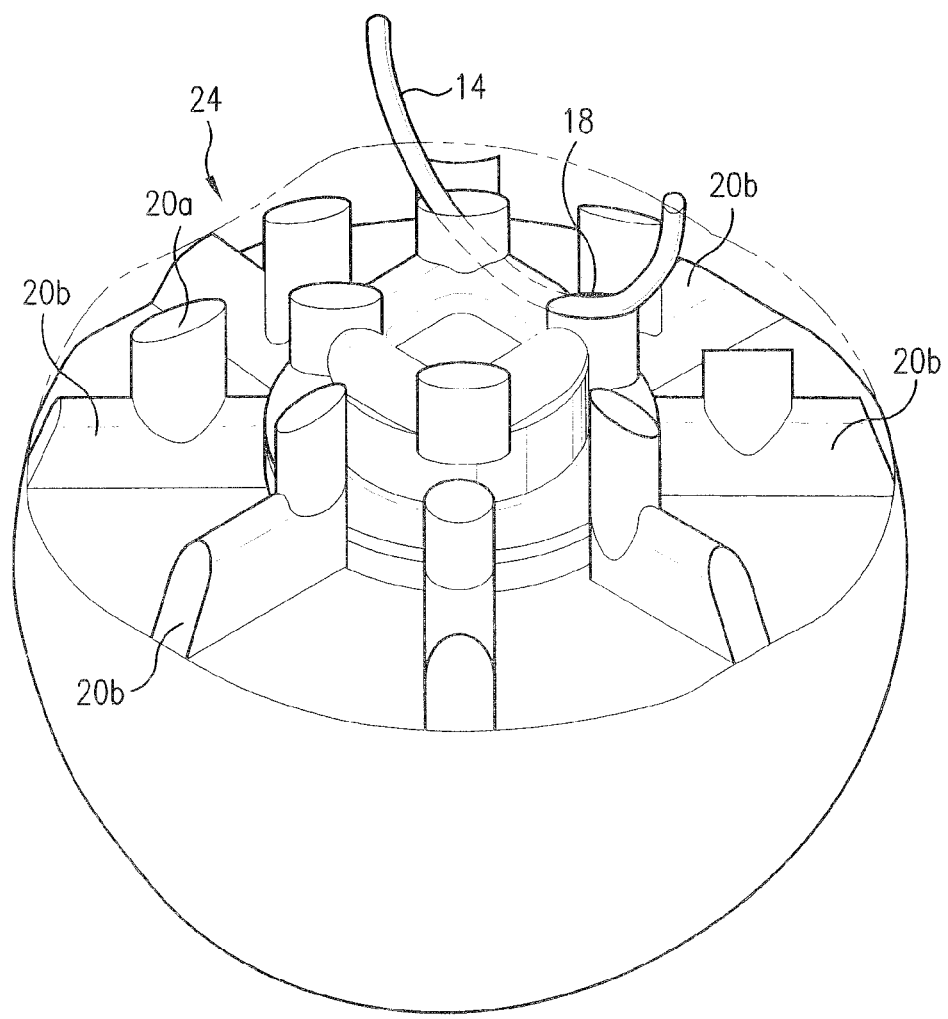
FIG. 8 is a perspective cut away view of the implant of the first preferred embodiment showing the tunnels and chimneys inside the anterior portion.
Figure 9:
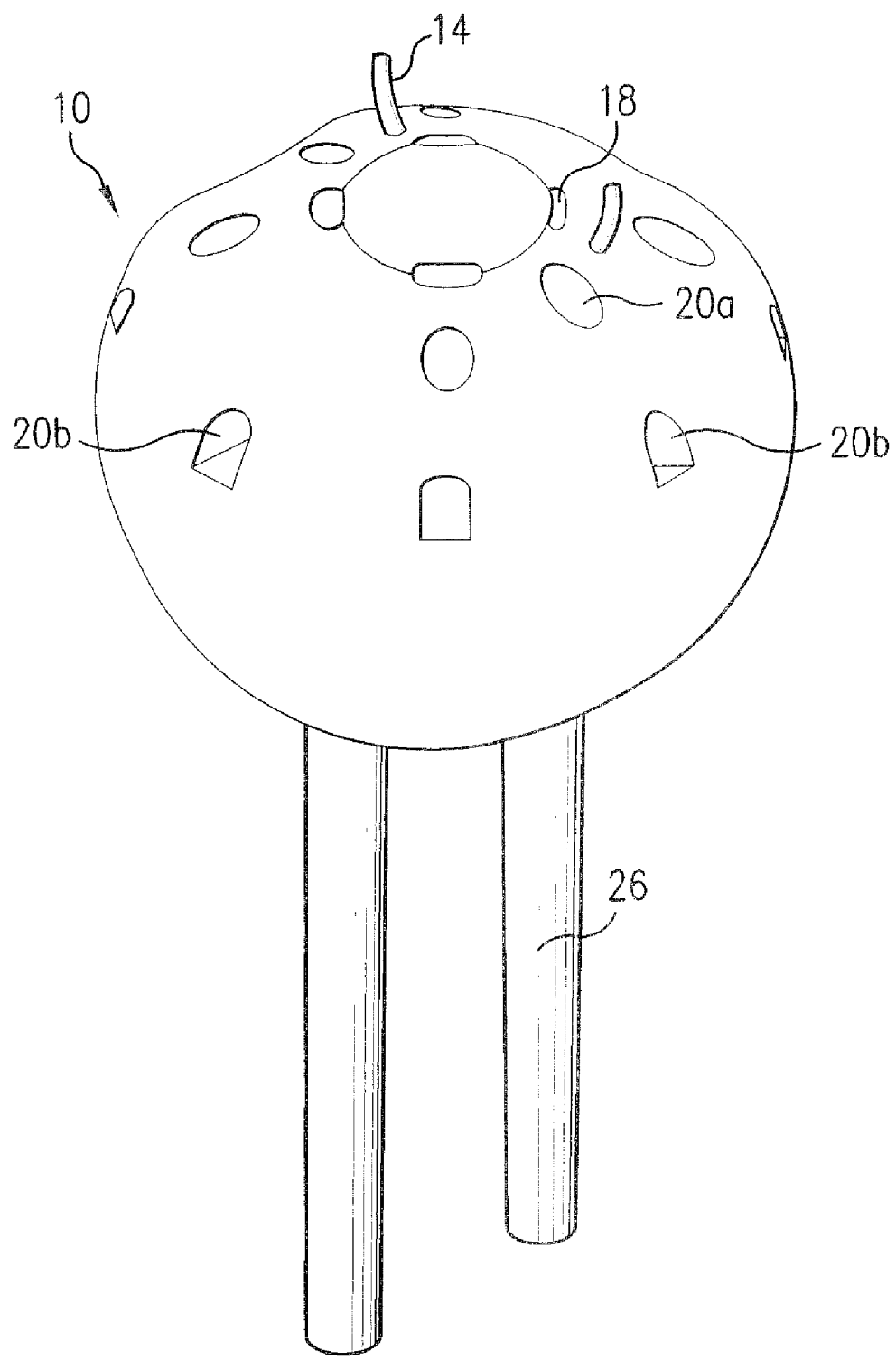
FIG. 9 is a prospective view of the implant of the second preferred embodiment.

As generally discussed above, the implant 10 is sutured to the patient's ocular muscles which are placed over the implant 10 once it is inserted into the orbit. As shown in FIG. 8, the sutures 14 are passed through tunnels 18 within the implant. As seen in FIG. 6, the first preferred embodiment comprises four suturing tunnels 18, and sixteen chimneys 20a, 20b in the anterior portion 22. A first set of eight of the chimneys 20a have their entrances open to the anterior side of the anterior portion 22, and a second set of eight of the chimneys 20b have their entrances open around the circumference of the anterior portion 22 so that direction of the second set of chimneys 20b is perpendicular to the direction of the first set of chimneys 20a. In the preferred embodiment, all of the first set of chimneys 20a interconnects with all of the second set of chimneys 20b to form a network of chimneys 20a, 20b inside the implant.

As discussed above, the tunnels 18 create voids within the implant which are adapted for the invasion of body fluids so that they progressively host the formation of new tissue that will secure the implant 10 to the muscles and covering tissue. The hollow chimneys 20a, 20b of the first embodiment are also adapted for the invasion of body fluids so that they progressively host the formation of new tissue that will secure the implant 10 to the patient's muscles and tissue. The result is that the implant 10 is less likely to migrate or dislodge once well sutured to the muscles, and once all muscles and covering tissue are healed and adhered to the implant 10. If additional stability is needed, chimneys 20c may be formed in the posterior portion 24 of the implant 10 as shown in FIGS. 16 and 17. Chimneys 20c may internally connect with the chimneys 20a, 20b of the anterior portion 22.

Second Preferred Embodiment

Figure 12:
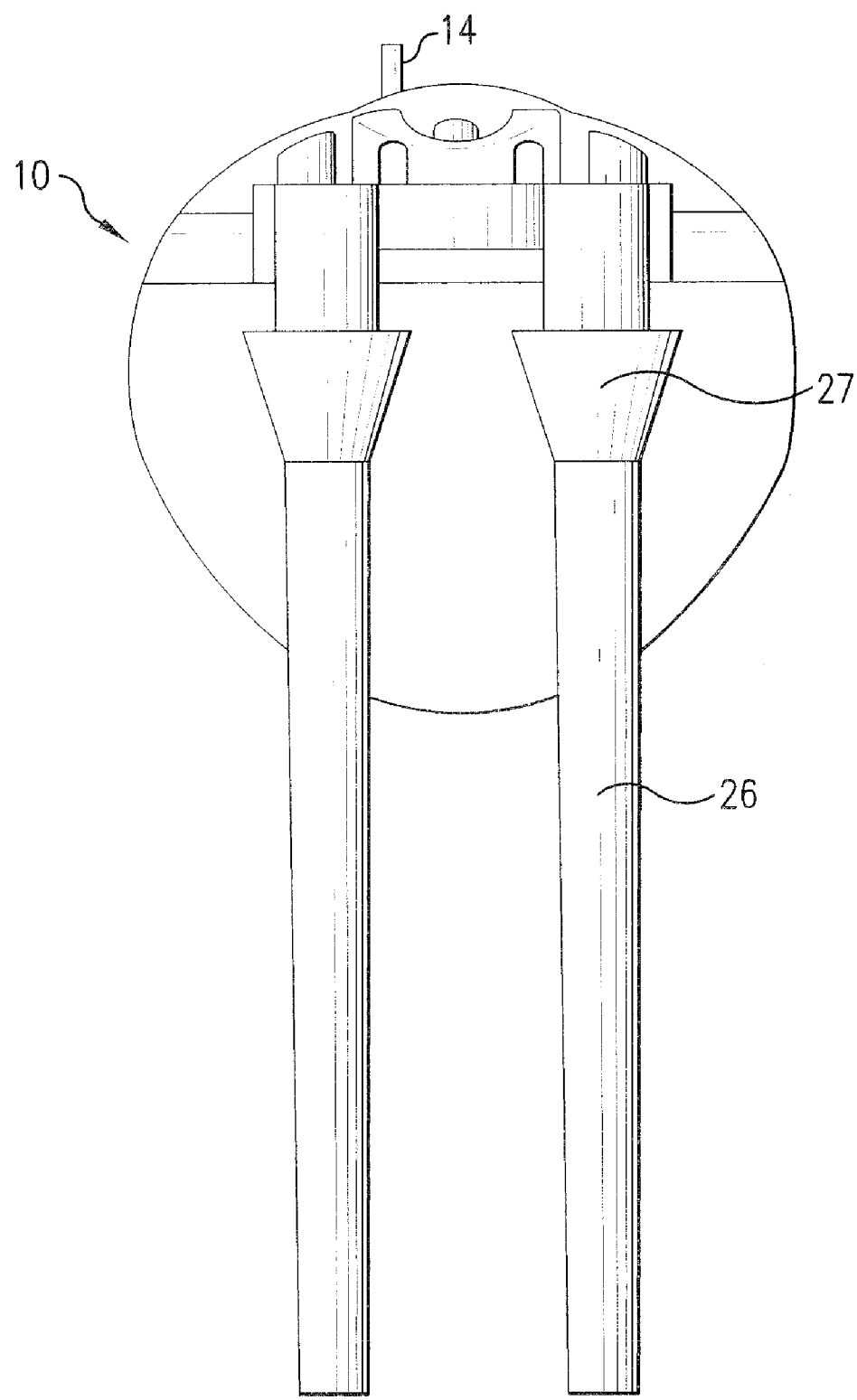
FIG. 12 is a cut away view of the implant of the second preferred embodiment showing the tentacles inside the implant (with reference to its position in a patient's right orbit)
Figure 12A:
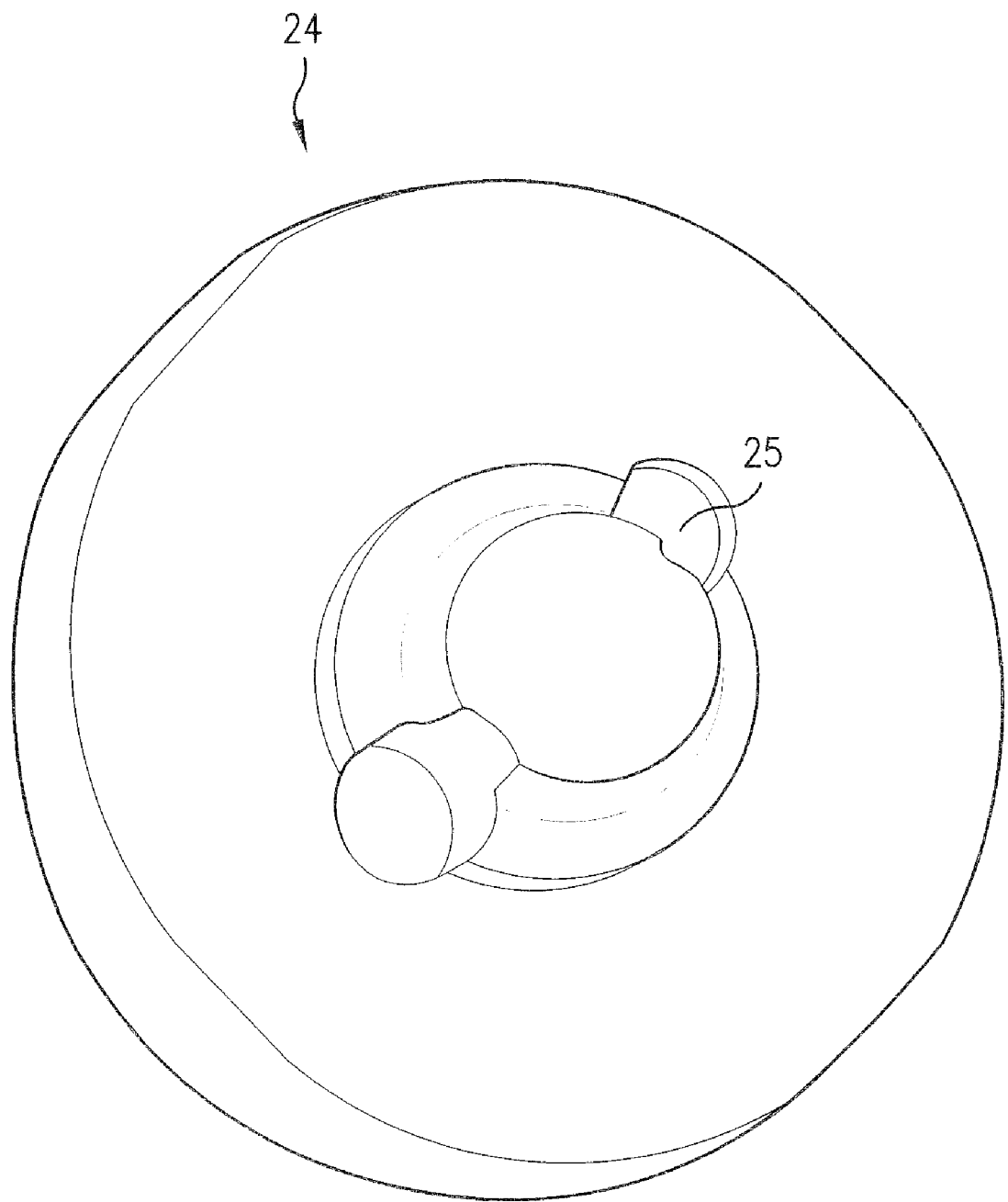
FIG. 12a is a perspective view of the posterior portion of the implant of the second preferred embodiment showing the holes which are adapted to receive the tentacles.

FIGS. 9-12 and 12a show a second preferred embodiment of the present invention which comprises all of the general features of the invention described above in addition to the features described below. The second preferred embodiment is comprised of a biomaterial that is elastomeric or an elastomer polymer such as silicone. In this embodiment, the anterior portion 22 and posterior portion 24 are adapted to be snapped together, since silicone cannot be welded. The preferred means for combining the two pieces in this embodiment is shown in FIGS. 12 and 12a, wherein tentacles 26 that are attached to the anterior portion 22 are placed through corresponding openings 25 in the posterior portion 24. The tentacles 26 have an enlarged portion 27 which cannot easily be removed from the openings 25 after being inserted into the openings 25. Once inserted into the openings 25, the enlarged portions 27 lock or snap the two portions 22, 24 together. Preferably there are two tentacles 26 so that during assembly, proper positioning of the pieces will be made easier because the anterior portion 22 can only be combined with the posterior portion 24 in two orientations, both of which correctly align the astigmatic shape and one of which correctly aigh the off-center conical elongation of the implant 10. Any portion of the tentacles 26 extending beyond the outer surface of the posterior portion 24 will be cut so as to make the implant 10 posterior surface flush with the tentacles 26.

Figure 10:
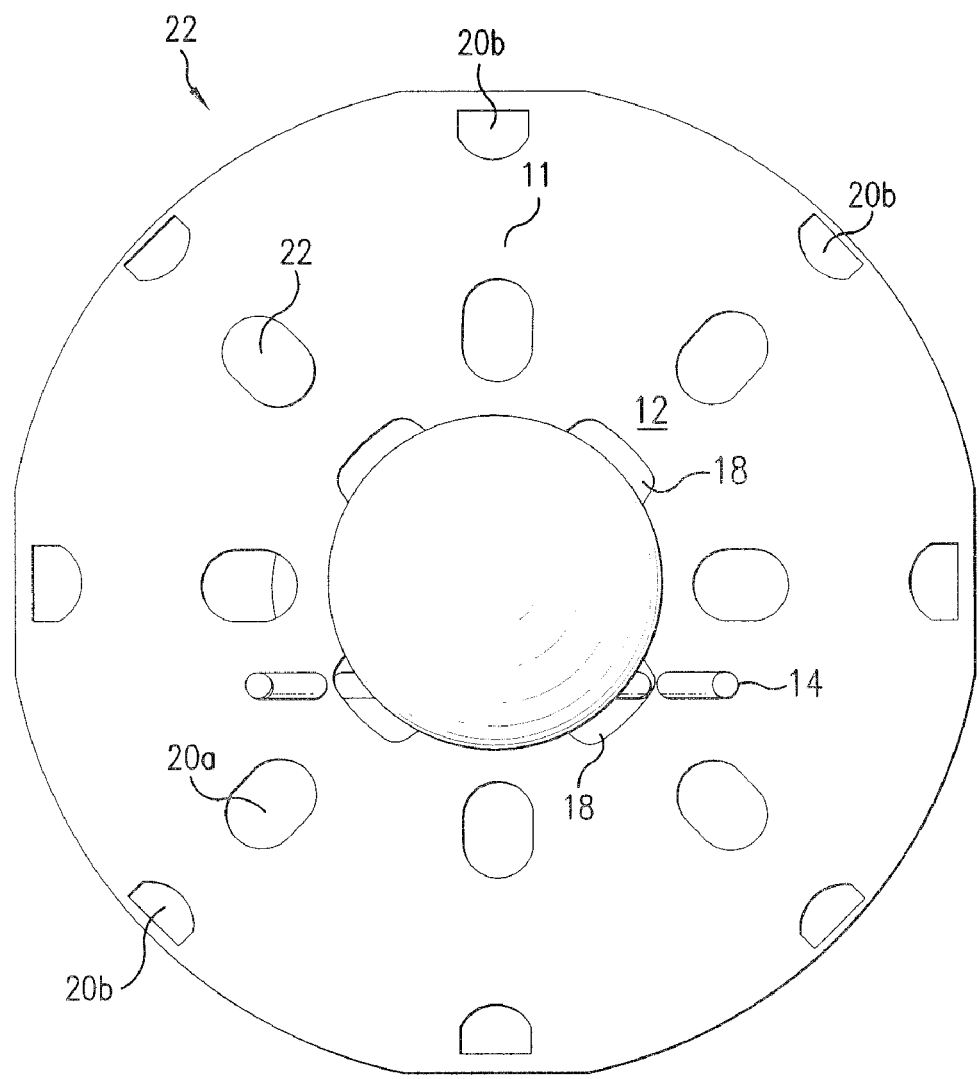
FIG. 10 is a side elevational view of the anterior portion of the implant of the second preferred embodiment (with reference to its position in a patient's right orbit)
Figure 11:
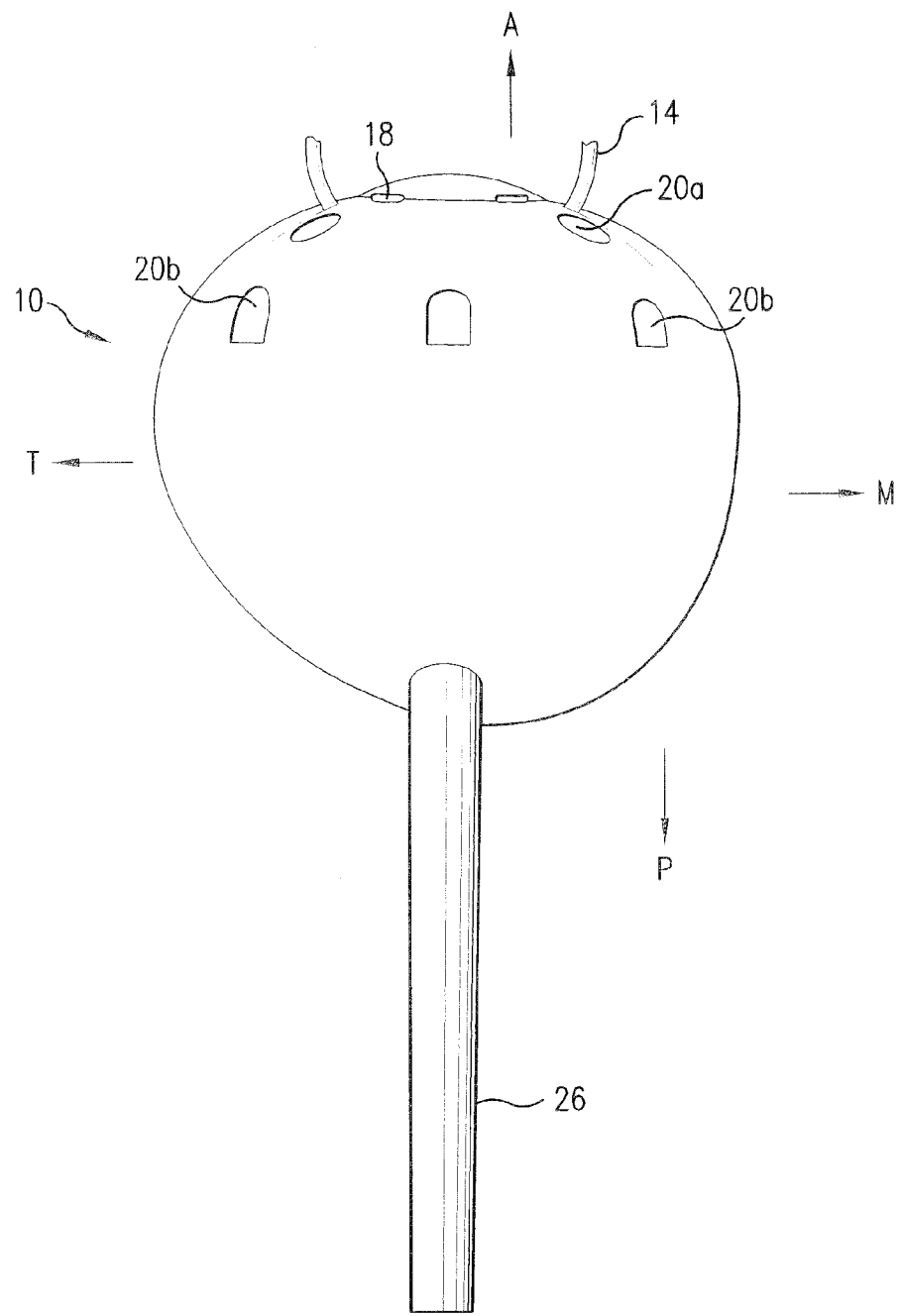
FIG. 11 is a bottom view of the implant of the second preferred embodiment (with reference to its position in a patient's right orbit) showing the tentacles for connecting the two pieces.

As seen in FIG. 10, the second preferred embodiment comprises four suturing tunnels 18 and fourteen chimneys 20a, 20b. As with the first preferred embodiment, some of the chimneys 20a, 20b extend at right angles to other chimneys 20a, 20b, and some of the chimneys 20a, 20b may connect with each other. This second preferred embodiment comprises fewer chimneys 20a, 20b than the first embodiment because the tentacles 26 extending from the anterior portion 22 occupy area where the additional chimneys 20a, 20b are located in the first embodiment. However, despite the tentacles 26, it is possible to include additional chimneys 20a, 20b in this second embodiment if it is determined that added support for the implant 10 may be needed.

Further, if additional stability is needed, chimneys 20c may be formed in the posterior portion 24 of the implant 10 as shown in FIGS. 16 and 17. Chimneys 20c may internally connect with the chimneys 20a, 20b of the anterior portion 22.

Third Preferred Embodiment

Figure 14:
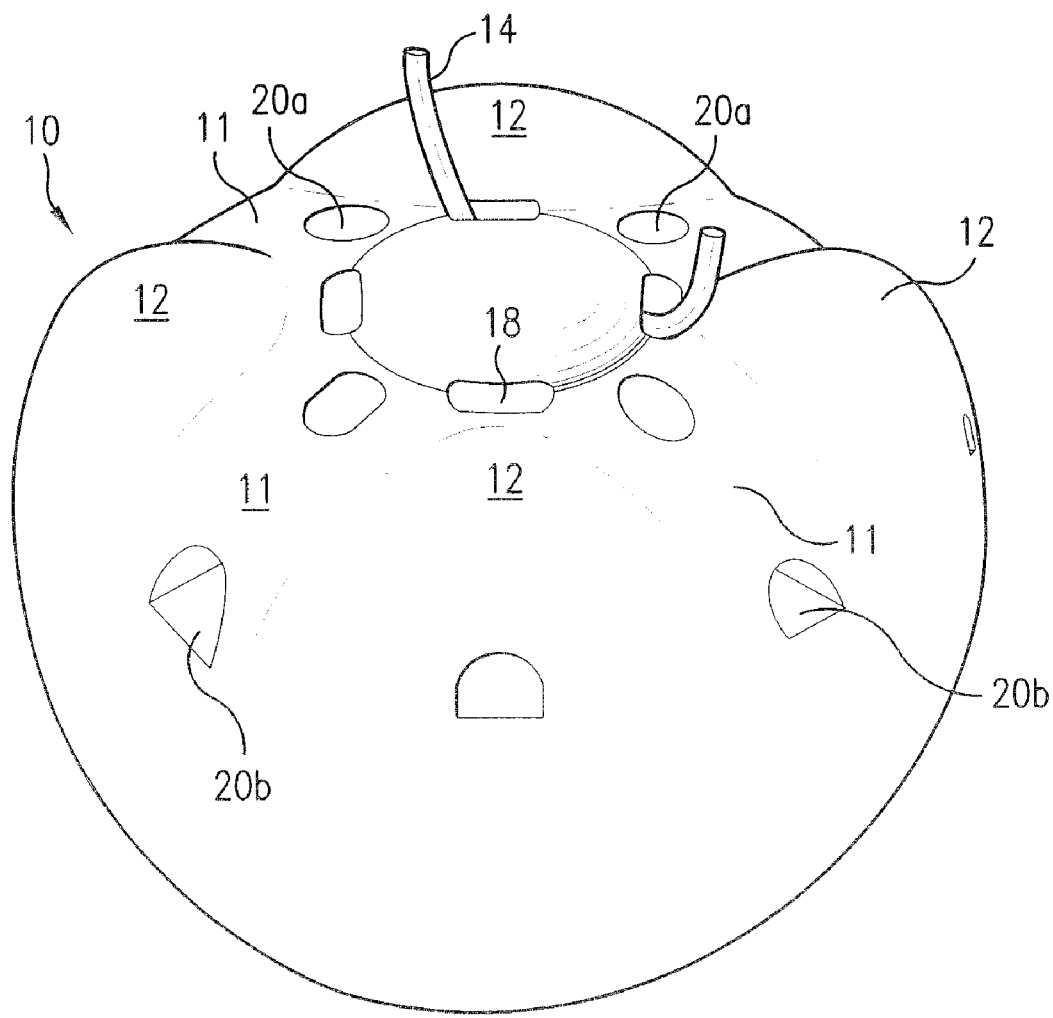
FIG. 14 is a perspective view of the third embodiment of the implant of the present invention showing the mounds and valleys.

FIG. 14 shows a third preferred embodiment of the implant 10 of the present invention wherein the valleys 11 and mounds 12 are more pronounced than in the first two embodiments. This embodiment can be manufactured with the characteristics of either the first or the second embodiment, with the only difference being the increased definition of the valleys 11 and mounds 12 on the anterior portion 22. The third preferred embodiment is still a quasi-sphere, however, the larger valleys 11 and mounds 12 help to increase the keying of the implant 10 on the ocular prosthesis for more motility and reduce the potential for rotation of the ocular prosthesis. The third preferred embodiment does not have an astigmatism in the anterior portion 22 because of the more pronounced valleys 11 and mounds 12. The third embodiment is not as likely to work well with stock prosthesis because of the more pronounced valleys 11 and mounds 12.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is:

1. An orbital implant device adapted for fitting into a patient's orbit, said orbit having a medial side, a temporal side, a posterior side, an anterior side, a superior side, and an inferior side, all with reference to the implant's position in the patient's orbit, said implant device comprising:
   an anterior side, a posterior side, a medial side, a temporal side, a superior side, and an inferior side, all said sides corresponding to the respective sides of the patient's orbit;
   a finite number of openings adapted for receiving sutures and for receiving bodily fluids and in growing tissue; and
   the implant having an anterior portion and a posterior portion;
   the implant having a quasi-spherical shape defined by a first elongation, the first elongation of the implant toward the medial side of the posterior side;
   the posterior portion of the implant is conically elongated off-center toward the medial side of the posterior side of the implant mimicking the natural shape of the orbit of a human eye which reduces the possibility that the anterior portion will become tilted upward or outward when implanted in the eye socket;
   an astigmatism toward the anterior side of the implant which is defined by a radius which is longer toward the medial and temporal sides of the implant, and which is shorter toward the superior and inferior sides of the implant which helps to provide motility for a prosthesis.

2. The orbital implant of claim 1 wherein the elongation is off center with respect to the anterior side.

3. The orbital implant device of claim 1 wherein the implant device is made of a polymer.

4. The orbital implant device of claim 3 wherein the polymer is acrylic.

5. The orbital implant device of claim 1 wherein the implant is manufactured as two separate parts and then combined together before being placed into the patient's orbit;
- wherein the two separate parts include an implant first portion and an implant second portion;
- wherein one of the openings is a first opening;
- wherein the implant first portion comprises a first section of the first opening and the implant second portion comprises a second section of the first opening;
- wherein the implant first portion is combined with the implant second portion so that the first section of the first opening and the second section of the first opening align to create the first opening.

6. The orbital implant device of claim 5 wherein the implant first portion and implant second portion are combined using ultrasonic welding.

7. The orbital implant device of claim 1 wherein the anterior side further comprises valleys and mounds which are adapted for keying with a prosthetic eye.

8. The orbital implant device of claim 1 wherein there are at least four openings which are adapted for receiving sutures and for receiving bodily fluids and in growing tissue.

9. The orbital implant device of claim 1 wherein there are at least fourteen openings.

10. An orbital implant device adapted for fitting into a patient's orbit, said orbit having a medial side, a temporal side, a posterior side, an anterior side, a superior side, and an inferior side, all with reference to the implant's position in the patient's orbit, said implant device comprising:
- an implant having an anterior portion and a posterior portion, said implant having a medial side, a temporal side, a superior side, and an inferior side, all said sides corresponding to the respective sides of the patient's orbit;
- the posterior end of the implant is conically elongated off-center toward the medial side of the posterior side of the implant mimicking the natural shape of the orbit of a human eye which reduces the possibility that the anterior end will become tilted upward or outward when implanted in the eye socket; and
- wherein the anterior portion and the posterior portion are manufactured as two separate parts and then combined together before being placed into the patient's orbit, wherein the anterior portion has a finite number of chimneys adapted for receiving bodily fluids and in-growing tissue, the anterior portion has a finite number of tunnels adapted for receiving sutures, the tunnels each having a diameter capable of receiving a needle and suture.

11. The orbital implant device of claim 10 wherein the implant device is made of acrylic.

12. The orbital implant device of claim 10 wherein the implant device is made of silicone.

13. The orbital implant device of claim 10 wherein the implant first portion and the implant second portion are combined using ultra-sonic welding.

14. The orbital implant device of claim 10 wherein the tunnels have a diameter between one and two millimeters.

15. The device of claim 1 wherein:
- the implant anterior portion and the posterior portion are manufactured as two separate parts and then combined together before being placed into the patient's orbit;
- an elevated portion on the posterior portion or the anterior portion;
- a corresponding indentation on the other of the anterior portion or the posterior portion that keys with the elevated portion to ensure proper alignment of the anterior portion with the posterior portion; wherein the elevated portion and the indentation can only fit together when properly aligned.

16. The device of claim 10 wherein:
- an elevated portion on the posterior portion or the anterior portion;
- a corresponding indentation on the other of the anterior portion or the posterior portion that keys with the elevated portion to ensure proper alignment of the anterior portion with the posterior portion; wherein the elevated portion and the indentation can only fit together when properly aligned.

* * * * *

UNITED STATES PATENT AND TRADEMARK OFFICE
CERTIFICATE OF CORRECTION

PATENT NO. : 7,988,730 B2  Page 1 of 1
APPLICATION NO. : 10/711695
DATED : August 2, 2011
INVENTOR(S) : Jean-Francois Durette It is certified that error appears in the above-identified patent and that said Letters Patent is hereby corrected as shown below:

Title page item [75] inventor: "Jean-Francios Durette" should be "Jean-Francois Durette".

Signed and Sealed this
Twenty-fourth Day of January, 2012

David J. Kappos
*Director of the United States Patent and Trademark Office*